US011148845B1

(12) United States Patent
Ellis

(10) Patent No.: US 11,148,845 B1
(45) Date of Patent: Oct. 19, 2021

(54) OSTOMY POUCH WASTE CHANNEL ACCESSORY

(71) Applicant: Revokable Trust for Benny R. & Beverly M. Ellis, Springfield, MO (US)

(72) Inventor: Benny R. Ellis, Springfield, MO (US)

(73) Assignee: Revokable Trust for Benny R. & Beverly M. Ellis, Springfield, MO (US)

( * ) Notice: Subject to any disclaimer, the term of this patent is extended or adjusted under 35 U.S.C. 154(b) by 0 days.

(21) Appl. No.: 17/112,970

(22) Filed: Dec. 4, 2020

(51) Int. Cl.
*A61F 5/445* (2006.01)
*A61F 5/44* (2006.01)
*B65B 69/00* (2006.01)

(52) U.S. Cl.
CPC ........ *B65B 69/0016* (2013.01); *A61F 5/4404* (2013.01); *A61F 5/445* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,299,431 A | | 10/1942 | Shirey | |
| 2,568,857 A | * | 9/1951 | Jacobs | A61F 5/442 4/239 |
| 2,801,424 A | * | 8/1957 | Mercer | A61B 10/007 4/661 |
| 2,894,263 A | * | 7/1959 | Kunkel | E03D 11/00 4/420 |
| 3,466,145 A | * | 9/1969 | Van Duyne | A61B 10/007 422/566 |
| 3,500,480 A | * | 3/1970 | Michal, Jr. | E03D 11/025 4/301 |
| 3,625,654 A | * | 12/1971 | Van Duyne | A61B 10/007 600/574 |
| 3,822,419 A | * | 7/1974 | Wilson, Sr. | E03D 13/00 4/144.4 |
| 4,137,573 A | * | 2/1979 | Kroeger | A61B 10/007 248/214 |
| 4,203,169 A | * | 5/1980 | Dale | A61B 10/007 4/144.1 |
| 4,280,498 A | | 7/1981 | Jensen | |
| 4,282,611 A | * | 8/1981 | O'Day | E03D 11/025 4/144.1 |

(Continued)

FOREIGN PATENT DOCUMENTS

BR 202013027029 4/2019
CA 3013453 A1 8/2017
(Continued)

*Primary Examiner* — Guy K Townsend
(74) *Attorney, Agent, or Firm* — Shah IP Law, PLLC

(57) ABSTRACT

An apparatus for assisting an emptying procedure of an ostomy pouch includes a conduction structure providing a channel for conducting waste material from the ostomy pouch when the ostomy pouch is being emptied and a support structure for stabilizing the conduction structure without requiring that a user uses a hand to hold the support structure during the emptying procedure. The top opening of the conduction structure is sized so that an emptying port of the ostomy pouch fits inside the top opening. A length of the conduction structure is predetermined such as to reduce a splash caused by waste material exiting a bottom opening of the conduction structure into a water layer of a toilet bowl.

20 Claims, 6 Drawing Sheets

(56) References Cited

U.S. PATENT DOCUMENTS

| | | | | |
|---|---|---|---|---|
| 4,285,076 A * | 8/1981 | Dickstein | A61F 5/445 | |
| | | | 4/300.2 | |
| 4,932,083 A * | 6/1990 | Arozena | E03D 11/025 | |
| | | | 4/144.1 | |
| 4,995,410 A | 2/1991 | Lash | | |
| 5,060,317 A * | 10/1991 | Bertelsen | A61B 10/007 | |
| | | | 4/144.2 | |
| 5,148,553 A * | 9/1992 | Jermann | A47K 11/12 | |
| | | | 4/144.1 | |
| 5,276,925 A * | 1/1994 | Blaha | E03D 11/025 | |
| | | | 4/300.3 | |
| 5,503,633 A * | 4/1996 | Saunders | A61F 5/44 | |
| | | | 4/340 | |
| 5,671,485 A * | 9/1997 | Middlestead | E03D 9/00 | |
| | | | 248/99 | |
| 5,737,779 A * | 4/1998 | Haddock | E03D 13/00 | |
| | | | 4/301 | |
| 5,819,331 A * | 10/1998 | Miuccio | E03D 11/025 | |
| | | | 4/341 | |
| 6,132,408 A | 10/2000 | Lutz | | |
| 6,151,972 A * | 11/2000 | Venter | A61B 10/00 | |
| | | | 4/144.1 | |
| 6,212,698 B1 * | 4/2001 | Stingley | A61B 10/007 | |
| | | | 4/144.1 | |
| 6,224,581 B1 | 5/2001 | Withers et al. | | |
| 6,237,654 B1 * | 5/2001 | Sheyer | B65B 69/0016 | |
| | | | 141/114 | |
| 6,434,762 B2 * | 8/2002 | Gordon | A61B 10/0038 | |
| | | | 4/315 | |
| 6,651,259 B1 * | 11/2003 | Hartman | A61B 10/007 | |
| | | | 4/144.1 | |
| D489,453 S * | 5/2004 | Sapyta | A61B 10/007 | |
| | | | D24/122 | |
| 6,754,914 B2 * | 6/2004 | Nakamura | A61F 5/445 | |
| | | | 4/144.1 | |
| 6,811,754 B2 * | 11/2004 | House | A61B 10/007 | |
| | | | 220/476 | |
| 7,350,529 B2 * | 4/2008 | Sarvis | B08B 9/08 | |
| | | | 134/104.2 | |
| 8,079,562 B1 * | 12/2011 | Denman | A61B 10/007 | |
| | | | 248/311.2 | |
| 8,091,848 B1 * | 1/2012 | Reed | A61B 10/007 | |
| | | | 248/311.2 | |
| 8,166,579 B2 * | 5/2012 | Mehta | E03D 13/005 | |
| | | | 4/144.1 | |
| 8,167,857 B2 | 5/2012 | James | | |
| 8,480,640 B2 | 7/2013 | Santimaw | | |
| 8,690,794 B1 * | 4/2014 | Gallardo | A61B 10/007 | |
| | | | 600/562 | |
| 9,194,115 B1 * | 11/2015 | Green | A47K 11/12 | |
| | | | 4/144.1 | |
| 9,492,308 B2 | 11/2016 | Plath | | |
| 9,605,420 B1 * | 3/2017 | Berger | E03D 13/00 | |
| | | | 4/144.1 | |
| 9,637,906 B1 * | 5/2017 | Charles | E03D 13/005 | |
| | | | 4/144.1 | |
| 10,004,630 B2 * | 6/2018 | Saitoh | A61F 5/451 | |
| | | | 4/449 | |
| 2004/0093665 A1 * | 5/2004 | Nakamura | A61F 5/451 | |
| | | | 4/449 | |
| 2004/0267158 A1 * | 12/2004 | Paasch | A61B 10/007 | |
| | | | 600/573 | |
| 2006/0096016 A1 | 5/2006 | Krowl | | |
| 2006/0237039 A1 | 10/2006 | Sarvis | | |
| 2008/0306460 A1 | 12/2008 | Lund et al. | | |
| 2013/0110059 A1 * | 5/2013 | Kossow | A61F 5/4556 | |
| | | | 604/329 | |
| 2016/0310313 A1 * | 10/2016 | Saitoh | A61F 5/451 | |
| | | | 4/449 | |
| 2018/0008238 A1 * | 1/2018 | Paige | A61B 10/0058 | |
| | | | 422/566 | |
| 2020/0046543 A1 | 2/2020 | Scalise et al. | | |
| 2020/0078207 A1 * | 3/2020 | Parr | A61F 5/455 | |
| | | | 4/449 | |

FOREIGN PATENT DOCUMENTS

| | | |
|---|---|---|
| CN | 210472365 U | 5/2020 |
| EP | 1541099 A1 | 6/2005 |
| ES | 1232195 | 9/2019 |
| GB | 2256125 A | 12/1992 |
| GB | 2482007 A | 1/2012 |
| GB | 2491161 B | 9/2017 |
| JP | 4091418 B2 | 5/2008 |
| JP | 3176440 U | 6/2012 |
| WO | 1996004872 A1 | 2/1996 |
| WO | 2019213762 A1 | 11/2019 |

* cited by examiner

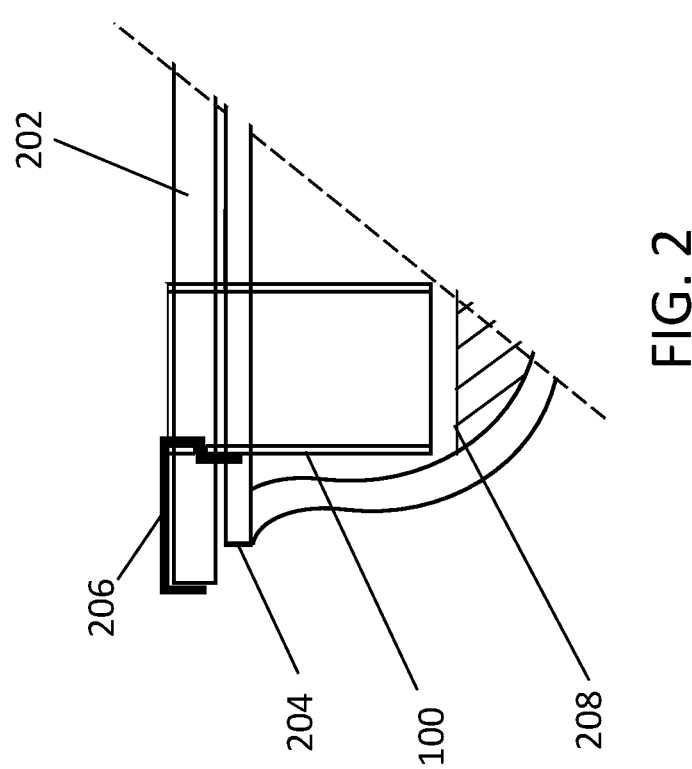

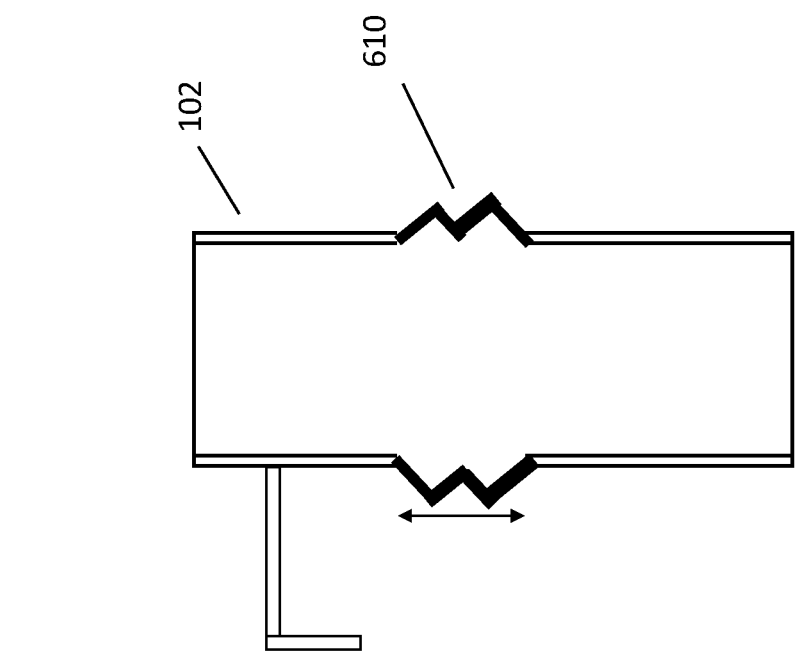
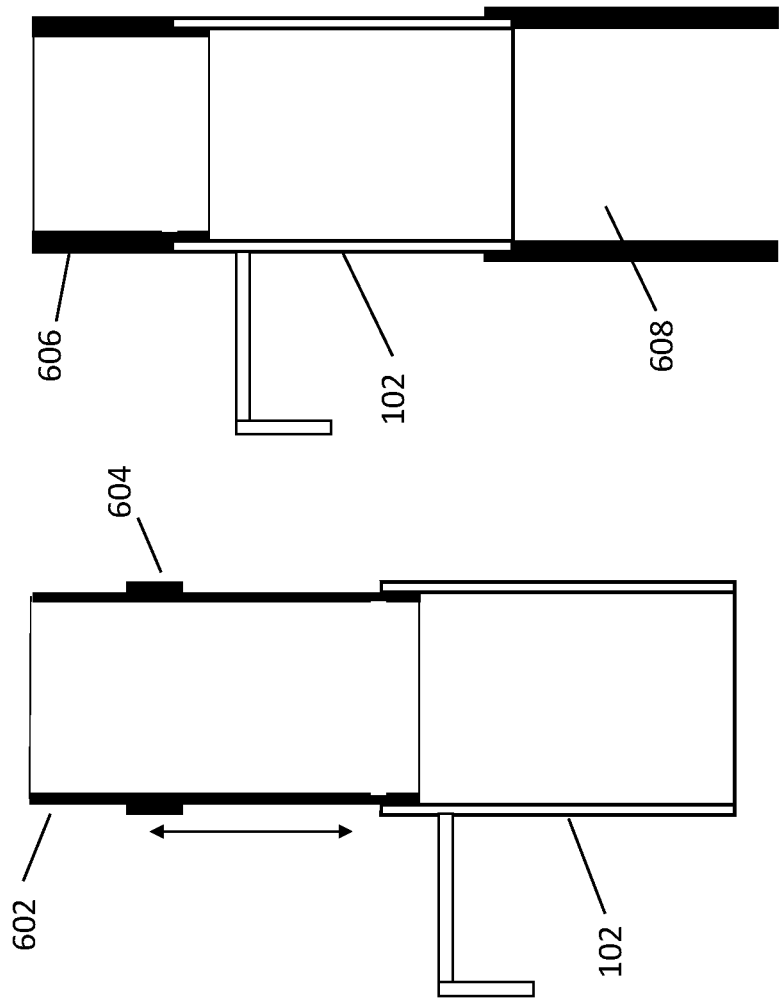
FIG. 6

OSTOMY POUCH WASTE CHANNEL ACCESSORY

CROSS-REFERENCE TO RELATED APPLICATIONS

None.

BACKGROUND

Field of the Art

This disclosure relates to an accessory device for assisting in emptying ostomy pouches. More specifically, an accessory apparatus provides a chute-like channel that is supported in a manner to permit both hands of a user to be used to empty an ostomy pouch into a toilet bowl in a manner that reduces splashing.

Discussion of the State of the Art

An ostomy is a surgical procedure that provides an opening, referred to as a stoma, in the abdomen of a patient, as attached to an organ such as an intestine, for purpose of eliminating body wastes into an attached ostomy pouch. An ostomy might be performed for any of various diseases or mishaps such as accidents. There are three categories of ostomies, as follows. A colostomy is used to collect waste from the large intestine, an ileostomy is used to collect waste from the small intestine, and a urostomy is used to collect urinary waste, and persons having an ostomy are often referred to as ostomates.

The location of the external hole (stoma) for an ostomy is typically inches to the left or right of the patient's navel. An ostomy pouch is connected around the stoma and hangs downward toward the patient's groin. The waste collected into the pouch from the colostomy or ileostomy is similar to a paste, being a soft mushy liquid rather than solid. Ostomy pouches are typically emptied six to eight times per day.

The pouches are typically emptied into a conventional toilet bowl that conventionally holds a preset amount of water used for flushing. The trajectory of the waste from an ostomy pouch causes an audible widespread splash in the toilet water and can also come into contact with the user's groin area and genitalia if no shield is present. The liquid, mushy, soft output, if uncontrolled, splashes the interior of the toilet bowl including areas above the level that is typically cleaned by the influx of water used to flush contents. The present invention addresses these problems.

Typical conventional methods of controlling the splash include, for example, a method of placing a cushioning layer or layers of toilet paper on the surface of the water in the bowl and/or draping toilet paper along the periphery of the top of the toilet bowl. Another method involves attempting to synchronize the flushing of the toilet as the pouch is emptied into the bowl. Yet another solution uses a toilet design having special construction to separately accommodate ostomy pouch servicing. Another entirely different approach is to empty the contents of an ostomy pouch into a water-soluble pouch and flush the filled pouch down a toilet.

The present invention considers that none of these conventional methods are particularly convenient and/or do not completely address the issue of splashing that occurs during the emptying of ostomy pouches.

SUMMARY

The present invention provides an alternative to conventional methods by providing an accessory device (or apparatus) having a channel through which ostomy pouch waste rushes while allowing a tidy, uninhibited flow from the pouch into the toilet bowl with minimal splashing. Because of the lower exit point provided by this channel, any splashing that may occur will be lower in the toilet bowl so that droplets of the splash will not escape the region of the bowl that is swept clean by the water used to flush the toilet.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

FIG. 2 illustrates how the invention is exemplarily supported by a toilet seat to permit the ostomy pouch contents to be discharged closer to the top of water in a toilet bowl.

FIG. 6 illustrates various exemplary configurations for providing extensions to the channel structure.

DETAILED DESCRIPTION

Figure 3:
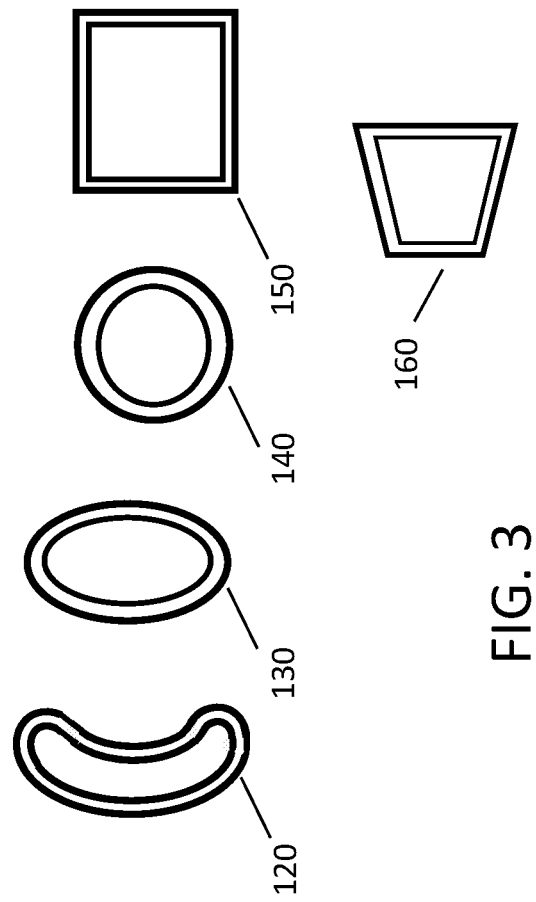
FIG. 3 illustrates various alternate shapes of the channel structure, as viewed from a top plan view.

The invention is described by reference to various elements herein. It should be noted, however, that although the various elements of the inventive apparatus are described separately below, the elements need not necessarily be separate. The various embodiment may be interconnected and may be cut out of a singular block or mold. The variety of different ways of forming an inventive apparatus, in accordance with the disclosure herein, may be varied without departing from the scope of the invention.

Generally, one or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices and parts that are connected to each other need not be in continuous connection with each other, unless expressly specified otherwise. In addition, devices and parts that are connected with each other may be connected directly or indirectly through one or more connection means or intermediaries.

A description of an aspect with several components in connection with each other does not imply that all such components are required. To the contrary, a variety of optional components may be described to illustrate a wide variety of possible embodiments and in order to more fully illustrate one or more embodiments. Similarly, although process steps, method steps, or the like may be described in a sequential order, such processes and methods may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, or method is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Alternate implementations are included within the scope of various embodiments in which, for example, functions may be executed out of order from that shown or discussed, including substantially concurrently or in reverse order, depending on the functionality involved, as would be understood by those having ordinary skill in the art.

Overview

The apparatus of the present invention provides a simple, convenient, and portable device that serves as a conduction channel to permit contents of an ostomy pouch to be directed into water in a toilet bowl sufficiently close to the surface of the water so as to enter with much reduced splashing. As will become clearer after the following description, the present invention thereby provides a portable and convenient accessory for ostomate patients that is also easily sanitized after each use.

Apparatus

Figure 1:
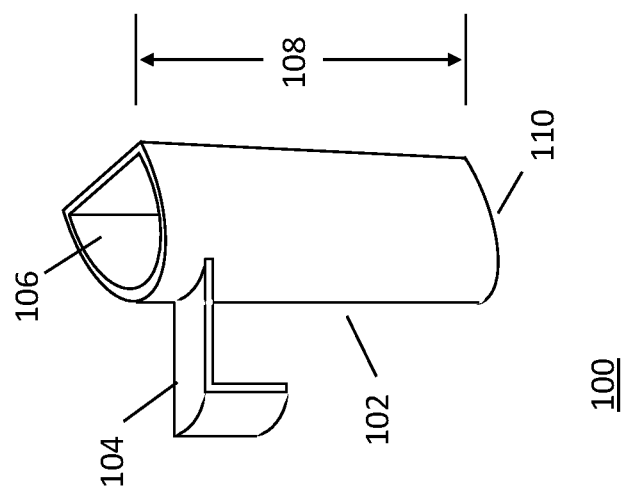
FIG. 1 illustrates a first exemplary embodiment of the invention as incorporating a support structure integral to the channel structure.

FIG. 1 illustrates a perspective view of the inventive apparatus 100 in accordance with an exemplary embodiment of the invention. In particular, FIG. 1 illustrates a device 100 for assisting an emptying procedure of an ostomy pouch in a manner that splashing is controlled without having to initially line the toilet bowl with strips of toilet paper or using other conventional methods for emptying ostomy pouches. The exemplary device 100 provides a conduction structure 102 that permits the pouch contents to exit closer to the surface of the toilet bowl water to reduce splashing when an ostomy pouch is emptied. By being nearer the bottom portion of the water surface, the conduction structure 102 also serves to intercept and reflect back downward any portions of the pouch discharge that would otherwise bounce off the water surface upward onto the interior of the toilet bowl above the level normally cleaned when the toilet is flushed, thereby reducing or eliminating the need to further clean the toilet bowl after emptying a pouch.

In an exemplary embodiment, a support structure 104 is attached to the conduction structure 102, providing a method of stabilizing the conduction structure 100 to the top rim of a toilet bowl or to a toilet bowl seat so that the user does not have to hold the conduction structure 102 or be concerned about stability of the device 100 during an emptying procedure. When used to empty an ostomy pouch, the discharge port of the pouch is placed into the top opening 106, and the contents of the pouch is pushed through the conduction structure 102 to exit from bottom opening 110. Therefore, the dimensions of the top opening 106 is predetermined to permit insertion of the discharge port of the ostomy pouch. FIG. 1 shows the support structure 104 as being on the cusp of the "D" shape and at an elevation slightly below the top of the conduction structure 102, but it should be clear that this location of the support structure 104 is not a limiting requirement of the device 100 since other locations on the conductions structure 102 would also permit the device to implement its intended function.

FIG. 2 exemplarily shows how the device 100 is supported by structure of a toilet bowl such as the toilet seat 202. It should be clear that the rim 204 of the toilet bowl could similarly be used for support structure 206 if the length of the device 100 and its support structure 104 were appropriately configured to be used with the rim 204 rather than the toilet seat 202.

It should also be clear from FIG. 1 and FIG. 2 that the present invention provides a simple, convenient, and portable device 100 that assists ostomates in overcoming the problem of splashing associated with emptying their ostomy pouches, using a manner and structure entirely different from any conventional method or device.

The exemplary device 100 shown in FIG. 1 shows a support structure 104 that at least suggests that it is permanently attached to the conduction structure 102 using, for example, attachment bolts or screws or by being integrally attached together during fabrication of the device 100. However, it should be clear that permanent attachment is not necessary and configurations in which the support structure 104 is detachable would provide a convenience that the device 100 could be broken down for reducing space needed for storage, as demonstrated by non-limiting examples to be described shortly relative to FIG. 4.

Additionally, the exemplary embodiment shown in FIG. 1 has a "D" shape when viewed from a top plan view, but such shape is not essential to the functioning of the device, and FIG. 3 shows alternate shapes including, but not limited to a "C" shape 120, an oval or elliptical shape 130, a circular shape 140, a rectangular shape 150, which would include a square shape if sides of the rectangle 150 are equal, and a trapezoidal shape 160. Whichever shape is used for the plan view, it should be clear that the dimension of the interior of the shape is predesigned for insertion of the exit port of the ostomy pouch. FIG. 1 suggests that the support 104 is located at a cusp of a shape used for the top plan view, but it should be clear that other locations of the support structure 104 around the periphery of the top plan view would permit intended functioning of the invention and might be more convenient for use of the device as dependent upon different shapes of toilet bowls and where the device is placed on any specific toilet bowl shape. Additionally, since using the device 100 for emptying an ostomy pouch when sitting on a toilet inherently means that space is typically tight for the user, the preferred shapes are the "D" and "C" shapes, since these two shapes conserve space when device 100 is placed against the user's abdomen.

FIG. 1 can also be used to explain another aspect of preferred embodiments of the invention in that the interior surface of the conduction structure 102 be smooth and preferably have a constant internal dimension throughout its length 108, for purpose of allowing easy cleanup after each use by simply rinsing the interior walls of the conduction structure 102. The conduction structure 102 can be formed with a material such as a metal or plastic resin that will make the conduction structure 102 rigid.

Alternatively, by using a flexible, rubber-like material, the conduction structure 102 can be fabricated to be compressible for storage in a pocket or purse or other carrying package when not in use while expanding to become at least semi rigid when extracted from a storage container, meaning that the structure becomes sufficiently rigid to form the intended shape that permits the ostomy pouch contents to be directed downward closer to the surface of the water in the toilet. Such compressible embodiments of the conduction structure 102 would be much more convenient for users who do not stay at home, since the compressible conduction structure 102 could then be discretely stowed in a carrying packet, such as a user's purse or other carrying method such as a pocket.

Figure 4:
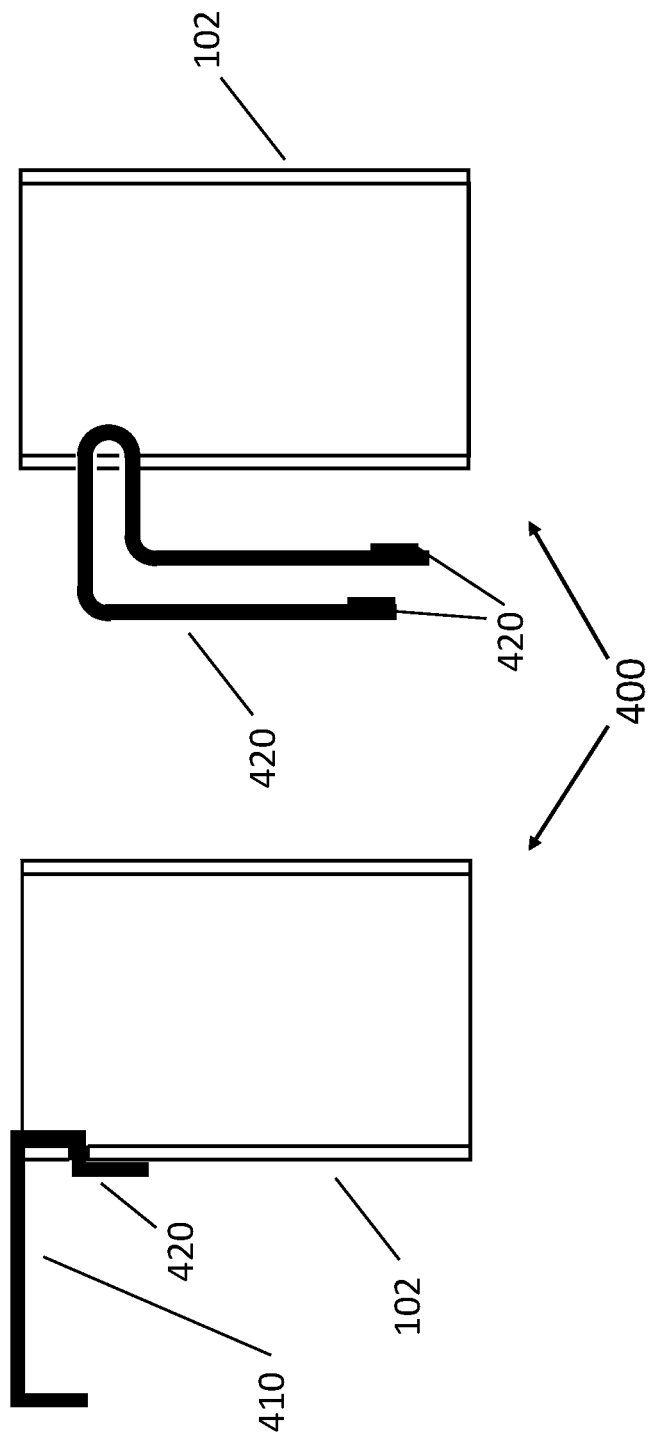
FIG. 4 illustrates two exemplary alternate methods of providing support for the channel structure using either the toilet bowl rim or the toilet seat.

FIG. 1 shows an exemplary embodiment in which the support structure 104 is implied as being affixed to the conduction structure 102. In contrast, FIG. 4 shows cross-sectional views 400 in which the support structure is not integral to the conduction structure 102. The embodiment in the left side of FIG. 4 shows a support structure 410 configured to be fitted into a slit opening in the sidewall of the conduction structure 102, where the shape and dimensions of this detachable support structure 410 are predetermined as fitting over either a rim of a toilet bowl or a toilet bowl seat as exemplarily illustrated in FIG. 2. The embodiment in the right side of FIG. 4 shows a support structure 420 comprising a flexible belt that is threaded through two slit openings in the conduction structure 102 and is predetermined in length to attach the conduction structure 102 to a toilet seat using, for example, a Velcro fastener 420 or other attachment mechanism to tie or otherwise attach the two ends of the belt 420 together around the toilet seat.

Either of the detachable mechanisms exemplarily shown in FIG. 4 can be viewed as another potential feature of the present invention providing a benefit that such detachable mechanisms permit a volume deduction for storage when the support structure is detached, which would be particularly useful in combination with a conduction structure 102 that is compressible.

Figure 5:
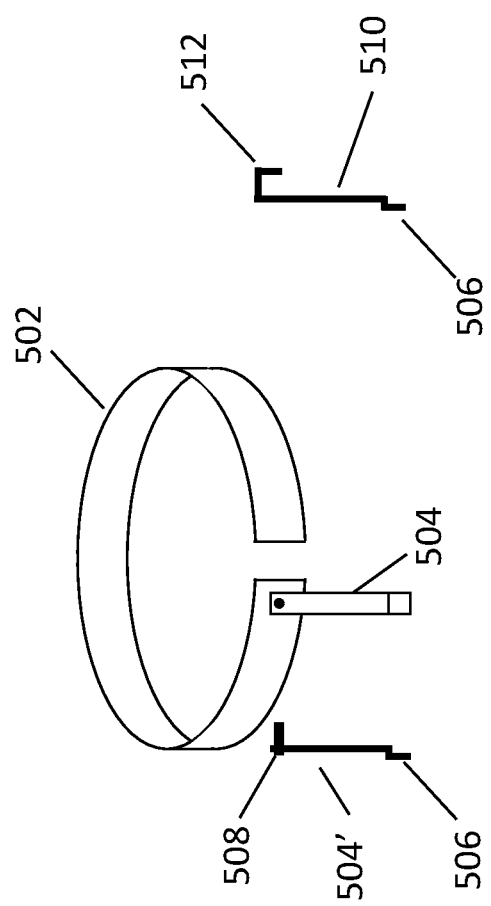
FIG. 5 illustrates two exemplary alternate methods of providing support for the channel structure without using the toilet structure.

FIG. 5 shows how the conduction structure 102 can be used in a manner such that support is provided without relying on parts of a toilet. In this method, a harness or belt 502 provides an attached support 504 that is configured to provide support for a conduction structure 102. The cross-sectional view 504' shows an exemplary attachment fitting 506 similar to that shown in the exemplary embodiment shown in the left side of FIG. 4. It should be clear that this attachment 506 could also be configured to support the exemplary embodiment shown in the right side of FIG. 4 if modified to incorporate at least one slit that would permit the strap 420 to be attached to attached support 504. The attachment 508 to belt 502 could be a rivet, bolt, even a simple hook that would permit the holder 504' to be attached to the belt 502.

The right side of FIG. 5 shows a variation to the embodiment shown in the left side of FIG. 5, in which the attachment 512 to a belt is simply a hook 512 that can be hooked over the user's existing belt, thereby providing an embodiment that eliminates the harness or belt 502. The embodiments of FIG. 5 demonstrate how a conduction structure 102 of the invention can be used without relying on parts of a toilet bowl for support as well as demonstrating how a user can conveniently empty their ostomy pouch from a standing or squatting position without having to attach the conduction structure 102 to a toilet bowl, although it should be clear that such embodiments may suggest that the length dimensions 108 of the device exemplarily shown in FIG. 1 may require modification, depending upon how a user intends to use the device. The various non-limiting examples of support mechanisms should demonstrate how the present invention provides a benefit of convenience to an ostomate user by permitting their ostomy pouches to be emptied without having to use a hand to hold the device 100 as a support during the emptying procedure.

Therefore, relative to length adaptations and returning briefly to FIG. 1, the device 100 in all embodiments is intended as having a top opening 106 of the conduction structure 102 sized so that an emptying port of the ostomy pouch fits inside the top opening 106. The length 108 of the conduction structure 102 is predetermined to provide a channel length sufficient to conduct the pouch contents close to the top surface of the toilet bowl water so as to reduce a splash caused by waste material exiting a bottom opening 110 of the conduction structure into the toilet bowl water layer.

The length 108 depends upon the user's preferred position used for emptying their ostomy pouch. Many users prefer to sit on the toilet bowl seat facing forward, essentially the common position for using a toilet. Other users prefer to sit on the front edge of the toilet bowl seat facing backwards. The channel length 108 would be similar for either of these two positions. For users that prefer to empty their ostomy pouch using a squatting or kneeling position facing the toilet bowl or a standing position, the length 108 could be adapted for these different preferences.

Therefore, although FIG. 1 shows the conduction structure 102 as a solid structure with fixed length 108, such embodiment is only exemplary since one of ordinary skill would readily understand that the conduction structure 102 could be configured to have adjustable length, using any of various possible mechanisms such as exemplarily shown in FIG. 6. As non-limiting examples, the conduction structure 102 could be configured as a sliding tube structure such that an inside tube structure 602 can slide inside an outer tube structure provided by conduction structure of device 100, thereby permitting the length 108 to be adjusted. The sliding motion of tube structure 602 is limited by a stop that limits the range of travel of the sliding structure 602. It should be clear that sliding extension 602 could be easily designed to be a bottom extender of device 100 (not shown in FIG. 6), although a bottom extender portion would preferably fit on the outside surface of device 100 in order to better provide a larger internal diameter so that ostomy pouch contents would be less likely to contact the sidewalls when being emptied, which means that the device 100 as extended could be more easily cleaned after a use.

This concept of maintaining optimal interior dimensions is better explained in the middle diagram in FIG. 6 that shows both an upper extender 606 and a lower extender 608, both of which are rigid or semi rigid (i.e., compressible, but which expand into a semi rigid shape) structures that are respectively configured to fit into either the upper or lower surface of conduction channel of device 100. Thus, it is noted that the upper extender 606 is shown as having a slightly narrower interior dimension that that of the conduction channel, and that the lower extender 608 is shown as having the same interior dimension. As explained above, this configuration of internal dimensions allows internal configurations providing minimal contact with sidewalls of contents being emptied from an ostomy pouch.

However, it should also be clear that extender portions 602, 606, 608 are not necessary components to permit the device 100 to perform its intended functions. It should also be clear that only one extender portion, rather that both an upper extender portion 606 and a lower extender portion 608 could be used. Additionally, it is noted that the lower extender portion 608 could serve as either an upper extender portion or a lower extended portion since its configuration provides the same internal dimension as that of the conduction structure of device 100.

The right diagram of FIG. 6 demonstrates yet another possible length adjustment, using an accordion-like structure 610 such that the length could be adjusted by pulling the ends of the device apart to stretch the length and pushing the ends together to shorten the length 108.

An important feature underlying the present invention is a capability to easily clean and sanitize the device after each usage. Therefore, it is important that the device 100 be constructed to have smooth surfaces that can be easily cleaned by, for example, simply rinsing in running water, particularly the surface of the inner walls of the conduction structure 102. Further, for configurations having capability of changing length 108 of the conduction structure 102 by adding one or more extender portion, it would be preferable that the extension capability be designed so that smooth surfaces be provided along the entire length of the extended configuration and that the inner dimensions are either constant or alternately slightly increase in the downward direction as each extender portion is added, as opposed to providing a narrowing internal dimension that would tend to contact the contents of an ostomy pouch being emptied.

Various configurations of the prototype shown exemplarily in FIG. 1 were constructed from a recycled plastic bottle, thereby demonstrating examples of the invention as having a rigid structure using such materials as a resin plastic or metal. However, it should be clear that the present invention is clearly not confined to rigid materials. Less rigid materials, such as a rubber-like resin, that would compress into a flattened profile that would fit in a pocket, purse, or other transport package and that would assume the desired shape when uncompressed, would provide a device configuration that is more convenient to carry by users who spend more time in public while being more discreet than carrying a rigid structure in a storage compartment.

Figure 7:
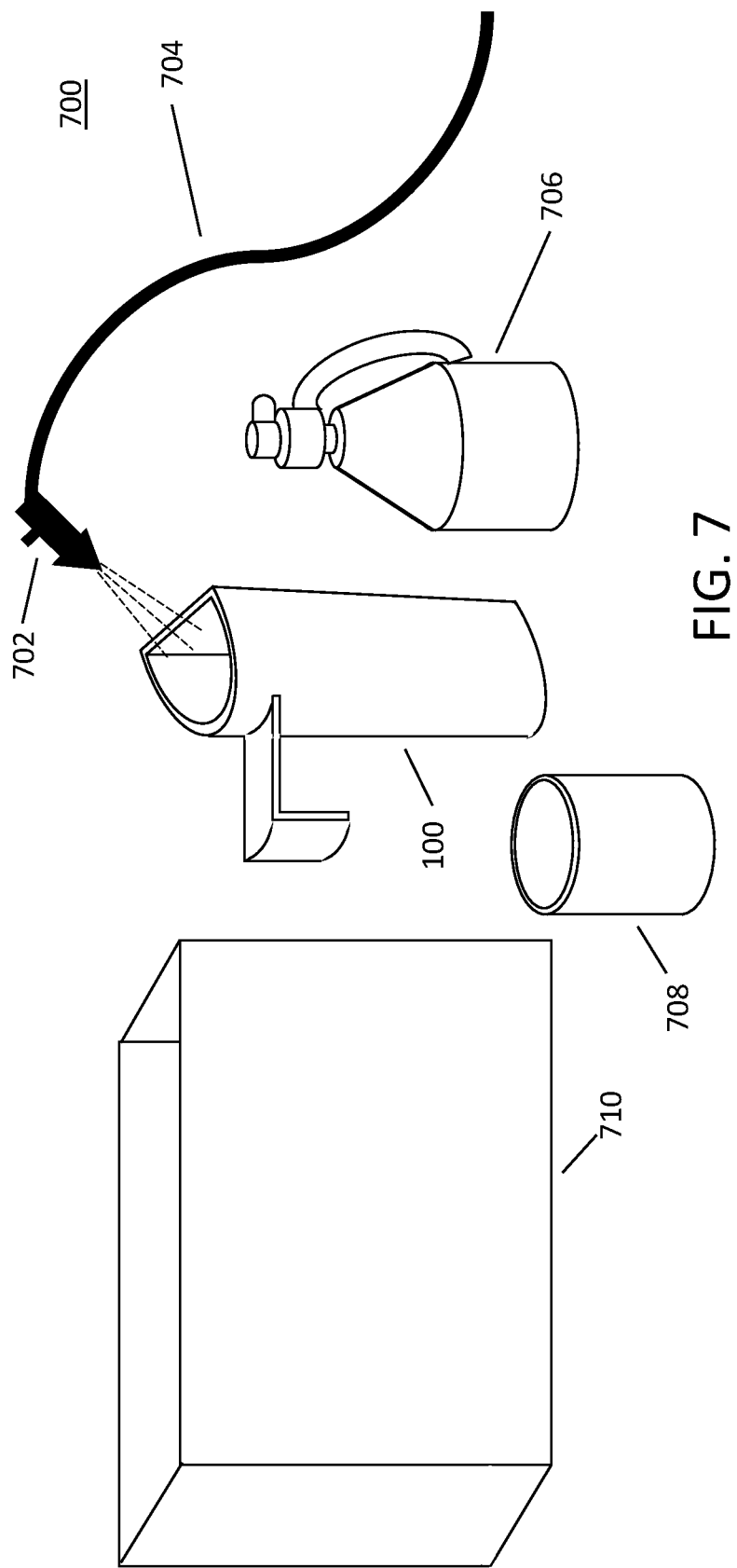
FIG. 7 illustrates exemplary configurations of kits supporting convenient storage and mobility of the invention by explaining how the channel structure can be easily cleaned by rinsing after using the invention for emptying an ostomy pouch.

FIG. 7 illustrates important aspects of the invention, regardless of which specific configuration is employed. As exemplarily shown in FIG. 7, device 100 is intended as being easily sanitized following each use, using, for example, running water to flush out at least the interior surface of the device. Such running water could be supplied, for example, by a spray nozzle 702 connected to a hose 704 connected to a water source such as the water pipe that supplies water to the toilet being used by the user for emptying their ostomy pouch. Such spray nozzle/hose combinations are well known as demonstrated by, for example, spray nozzles used in kitchen sinks or sprayers used to water house plants as having an adapter on the hose to be slipped over a water faucet spigot so that a common sink faucet can be used for watering house plants. A simple plastic bottle 706 with a sprayer head and filled with water could also be used for sanitizing device 100, or even a simple container 708 holding water to be selectively poured onto interior surfaces of the device 100 for cleaning after a use.

Thus, FIG. 7 illustrates another exemplary embodiment of the present invention as including a kit 700 of components carried in a carrier 710 and custom designed for convenience of each individual user's own preferences for using device 100 particularly when outside their normal living residence. A typical kit 700 could include, for example, a device 100 that is compressible and includes a detachable support structure such as exemplarily demonstrated in FIG. 4, thereby providing the user access to a device 100 with compact storage volume in addition to portability. Based on the user's preference the kit 700 could customized to include any or all of a sprayer/hose 702,704 that has a fitting to slip over a spigot of a common faucet head and/or an empty spray bottle 706 or empty container 708 that could also be compressible. Additional components such as any extender portions (see FIG. 6), preferably also constructed of compressible material to reduce storage volume, and perhaps one or more alternative support structures such as the belt support structure(s) exemplarily shown in FIG. 5, could be included in a user's customized kit 700. The customized kit 700 could also be sized to include a cloth or other fabric for drying off the device 100 after rinsing it, as well as other components the user prefers to have available relative to servicing their ostomy pouch such as, for example, packets having deodorant or sanitizer, which are sometimes used conventionally by ostomates when emptying and servicing of their ostomy pouch.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. An apparatus for assisting an emptying procedure of an ostomy pouch, the apparatus comprising:
    a conduction structure providing a channel for conducting contents from the ostomy pouch onto a surface of a water layer in a toilet bowl when the ostomy pouch is being emptied by squeezing out the contents by pressing on an outside surface of the ostomy pouch, the conduction structure having a top opening and a bottom opening and cross-sectional dimensions of the channel from the top opening to the bottom opening are constant throughout a length of the conduction structure; and
    a support structure for stabilizing the conduction structure without requiring that a user hold the support structure during the emptying procedure,
    wherein the top opening of the conduction structure is sized so that an emptying port of the ostomy pouch fits inside the top opening of the conduction structure so that contents of the ostomy pouch can be pushed out of the ostomy pouch into the channel of the conduction structure,
    wherein the length of the conduction structure is such as to terminate above a top surface of the water layer in the toilet and is predetermined such as to at least reduce a splash caused as the contents of the ostomy pouch exits the bottom opening of the conduction structure onto the surface of the water layer of the toilet bowl, meaning that the length of the conduction structure is predetermined so that any residual splash of the contents of the ostomy pouch exiting the bottom opening of the conduction structure occurs only in a surface region of the toilet bowl that will be cleaned by flushing water when the toilet is flushed, and
    wherein the apparatus is portable, meaning that it is small enough to be hand held so that it can be carried by a user in public without being noticed, while still being convenient for the user for emptying their ostomy pouch, meaning that the support structure permits the user to use both hands for squeezing out the contents of the ostomy pouch rather than having to steady the apparatus during the emptying procedure.

2. The apparatus of claim 1, wherein, in a top plan view, a top portion of the conduction structure is formed in a "D" shape.

3. The apparatus of claim 1, wherein, in a top plan view, a top portion of the conduction structure is formed in a "C" shape.

4. The apparatus of claim 1, wherein, in a top plan view, a top portion of the conduction structure is formed in one of a circular or elliptical shape.

5. The apparatus of claim 1, wherein the conduction structure comprises a rigid material.

6. The apparatus of claim 1, wherein the conduction structure comprises a pliable material such that the apparatus can be compressed for storage between uses.

7. The apparatus of claim 1, wherein the support structure is selectively detachable from the conduction structure so that the apparatus can be easily broken apart for portability and storage between uses.

8. The apparatus of claim 1, wherein the support structure comprises a rigid structure sized to fit over and be supported by a top surface of a toilet seat.

9. The apparatus of claim 1, wherein the support structure comprises a rigid structure sized to fit over and be supported by a top surface of a toilet bowl rim.

10. The apparatus of claim 1, wherein the support structure comprises a strap for strapping the apparatus to a toilet seat during the emptying procedure.

11. The apparatus of claim 10, wherein the strap comprises a velcro fastener for fastening the strap to the toilet seat.

12. The apparatus of claim 1, wherein the support structure comprises an adapter to support the conduction structure by selectively slipping the support structure over a belt being worn by the user.

13. The apparatus of claim 1, further comprising an extension portion, as selectively attachable to an opening of the conduction structure, a length of the extension structure predetermined to permit an emptying procedure from one of a standing position and a squatting position.

14. A kit, comprising:
    the apparatus of claim 1; and
    at least one device that provides a method for the user to rinse the apparatus after emptying their ostomy pouch.

15. An accessory device to assist in emptying contents of an ostomy pouch, the accessory device comprising:

a conduction structure providing a channel for conducting the contents from the ostomy pouch onto a surface of a water layer in a toilet bowl when the ostomy pouch is being emptied; and a support structure for stabilizing the conduction structure without requiring that a user hold the support structure during the emptying procedure, wherein a length of the conduction structure is such as to terminate above a top surface of the water layer in the toilet and is predetermined such as to at least reduce a splash caused by waste material exiting a bottom opening of the conduction structure onto the water layer of the toilet bowl, meaning that the length of the conduction structure is predetermined so that any residual splash of the contents of the ostomy pouch exiting the bottom opening of the conduction structure onto the water layer occurs only in a surface region of the toilet bowl that will be cleaned by flushing water when the toilet is flushed, wherein cross-sectional dimensions of the channel are constant throughout the length of the conduction structure, and wherein the accessory device is portable, meaning that it is small enough to be hand held so that it can be carried by a user in public without being noticed, while also being convenient, meaning that the support structure permits the user to use both hands for squeezing out the contents of the ostomy pouch rather than steadying the accessory device during the emptying procedure.

16. A kit, comprising:

a conduction structure providing a channel for conducting waste material from the ostomy pouch into a toilet bowl when the ostomy pouch is being emptied, the conduction structure configured to attach to a support structure that will stabilize the conduction structure without requiring that a user hold the support structure when the ostomy pouch is being emptied, wherein cross-sectional dimensions of the channel are constant throughout a length of the channel and wherein a length of the conduction structure is such as to terminate above a top surface of the water layer in the toilet and the length is predetermined so as to at least reduce a splash caused by waste material exiting a bottom opening of the conduction structure onto a water layer of the toilet bowl, meaning that the length of the conduction structure is predetermined so that any residual splash of the contents of the ostomy pouch exiting a bottom opening of the conduction structure onto the water layer occurs only in a surface region of the toilet bowl that will be cleaned by flushing water when the toilet is flushed; and at least one support structure that can be selectively attached to the conduction structure for emptying the ostomy pouch, wherein the kit is portable, meaning that it is small enough to be hand held so that it can be carried by the user in public without being noticed, while also being convenient, meaning that the support structure when attached to the conduction structure permits the user to use both hands for squeezing out the contents of the ostomy pouch rather than holding or steadying the conduction structure during the emptying procedure.

17. The kit of claim 16, further comprising at least one extender portion that can be selectively attached to an opening of the conduction structure to extend a length of the conduction structure for emptying the ostomy pouch.

18. The kit of claim 16, further comprising at least one device that provides a method for the user to rinse the conduction structure after emptying their ostomy pouch.

19. The kit of claim 18, further comprising a container to at least one of store and carry components of the kit.

20. A method of assisting a user in emptying an ostomy pouch, using the kit of claim 16, the method comprising:

removing the conduction structure and one of the at least one support structure from the kit;

attaching the support structure removed from the kit to the conduction structure;

supporting the conduction structure using one of the toilet seat and the toilet bowl rim;

inserting an exit port of the ostomy pouch into an upper opening of the conduction structure; and pressing the contents of the ostomy pouch into the conduction structure via the upper opening of the conduction structure.

\* \* \* \* \*